United States Patent [19]

Braber

[11] 4,345,963
[45] Aug. 24, 1982

[54] ASSEMBLY MACHINE FOR I.V. COMPONENTS

[75] Inventor: Robert J. Braber, Vernon Hills, Ill.

[73] Assignee: Abbott Laboratories, North Chicago, Ill.

[21] Appl. No.: 269,229

[22] Filed: Jun. 1, 1981

[51] Int. Cl.³ .............................................. B29B 3/00
[52] U.S. Cl. ..................................... 156/423; 29/458; 29/466; 29/786; 29/787; 29/793; 29/795; 156/294; 156/521; 156/559; 156/578; 198/479; 198/833
[58] Field of Search ............... 156/294, 423, 443, 521, 156/559, 578; 29/458, 466, 469, 757, 786, 787, 790, 793; 198/479, 833

[56] References Cited

U.S. PATENT DOCUMENTS

| Re. 29,448 | 10/1977 | Brown et al. | 156/294 |
|---|---|---|---|
| 3,334,550 | 8/1967 | Craig | 156/521 |
| 3,747,737 | 7/1973 | Brooke | 198/479 |
| 3,959,065 | 5/1976 | Ashcroft | 156/294 |
| 4,281,442 | 8/1981 | Senior et al. | 29/757 |

*Primary Examiner*—Jerome W. Massie
*Attorney, Agent, or Firm*—Robert L. Niblack; Neil E. Hamilton

[57] ABSTRACT

An apparatus and method for placing component parts on the ends of flexible tubing which is employed in an I.V. administration set. Flexible tubing is continuously supplied in a rectilinear manner and cut into predetermined lengths. These lengths have the ends thereof moved in a substantially transverse manner with respect to the original direction. Each end is then placed in a solvent-type solution and subsequently into a cavity of a component part. All of the foregoing functions are accomplished continuously and automatically in a device which employs a conveyor system for the cut tubing and a separate conveyor system for the component parts. The conveyors travel over a substantial elliptical pathway and along a horizontal axis. The upper conveyor is positioned with respect to the lower conveyor such that their pathways overlap a substantial distance. The upper conveyor provides a multiplicity of carrier members to which are fed and positioned predetermined cut lengths of flexible tubing. The carrier members have provided predetermined cut lengths of tubing which are held thereon by tubular holding portions. The holding portions extend from a pair of rotatable body members which after receiving the tubing therein are rotated by a camming action 90° so that the ends of the tubing are placed upwardly and also 90° with respect to their original rectilinear position. Simultaneously with this positioning of the tubing commodities such as I.V. components are fed into carrier members in the conveyor, beneath the conveyor or the cut tubing. The commodities will be fed into the carriers at the lower pathway and moved upwardly to the upper surface thereof. Simultaneously, the upwardly extending cut ends of the tubing will be moved from the upper surface of the upper conveyor to the lower surface thereof by suitable camming action. The ends of the tubing will be placed into a reservoir of adhesive material prior to being positioned in the respective commodities.

11 Claims, 19 Drawing Figures

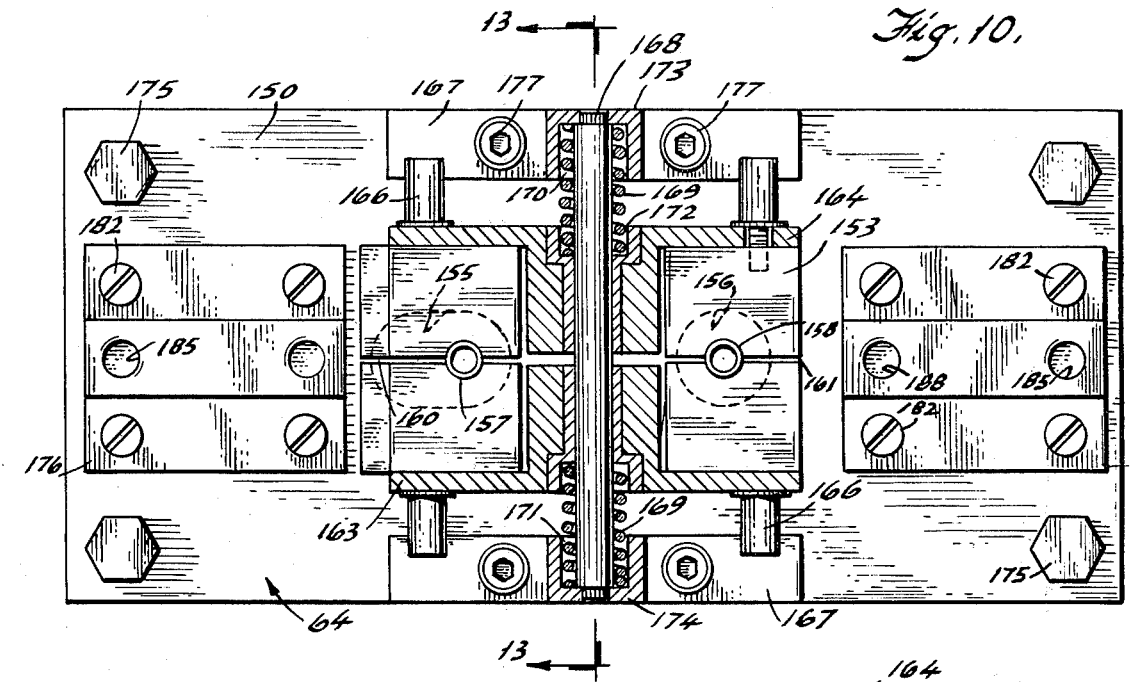
Fig. 10.
Fig. 11.  Fig. 12.
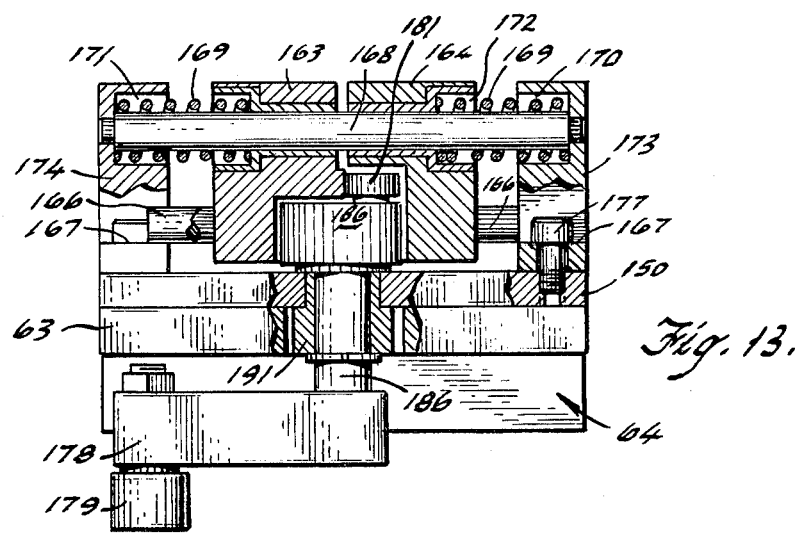
Fig. 13.

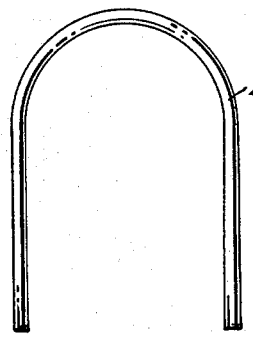
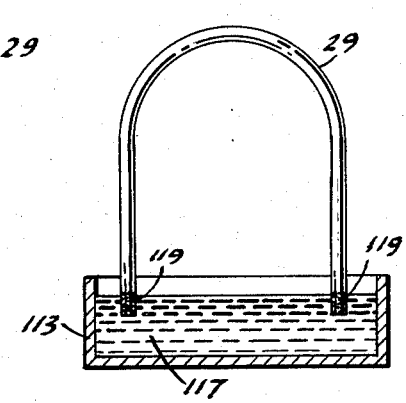
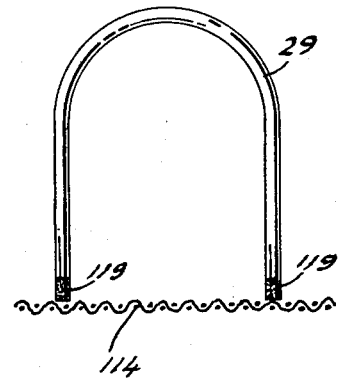
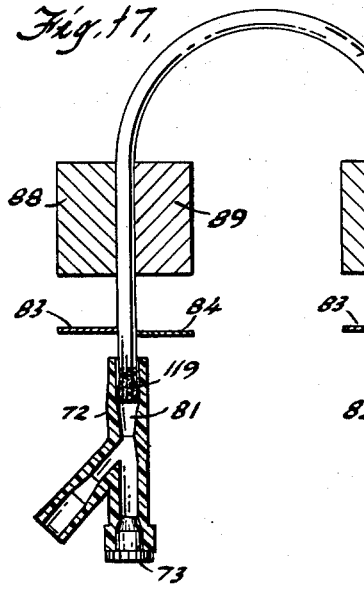
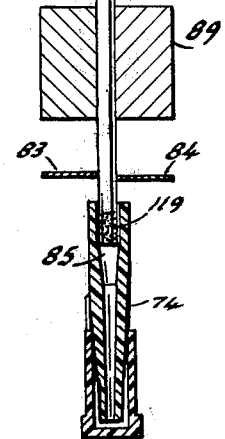
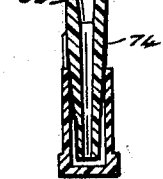
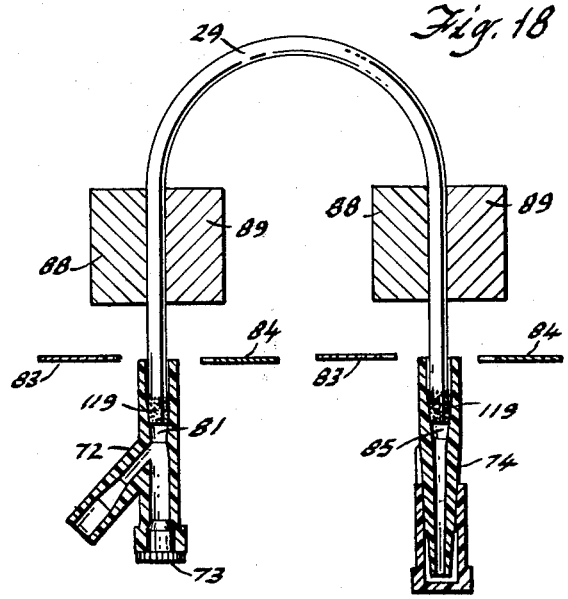

ASSEMBLY MACHINE FOR I.V. COMPONENTS

BACKGROUND OF THE INVENTION

This invention relates to an apparatus for assembling component parts to lengths of flexible tubing. More particularly, it relates to an apparatus and method for automatically securing component parts to lengths of flexible I.V. tubing in a manner such that the ends of the flexible tubing are turned at an angle of approximately 90° to the original position and with the ends so disposed they are automatically placed in different commodities thus resulting in a component part for an I.V. administration set.

The assembly of I.V. administration sets is for all practical purposes a manual operation. Tubing can be automatically cut by machine. However, after this procedure the remaining operation is usually accomplished by hand. This means the ends of the lengths of tubing must be aligned with and inserted into cavity portions in the commodities by hand. Prior thereto the ends will be dipped into an adhesive such as solvent, the excess solvent material removed and then the previously described insertion. The reason the foregoing procedure has only been accomplished by hand is that by nature of the flexible tubing, it is extremely difficult to position and handle other than by the human hand.

There is not presently available a fully automated assembly device which can accept I.V. tubing from a constant source such as a spool, cut it into predetermined lengths, bend it and then place the ends thereof after they are treated with an adhesive into various I.V. commodities. As explained previously, the prior art concerns itself with basically a manual procedure.

It is an advantage of the present invention to provide an apparatus and method for assembling component parts to lengths of flexible tubing at high production rates. Other advantages are an apparatus and method which can continuously receive and cut lengths of flexible I.V. tubing and place the ends thereof into various I.V. component parts at high production rates and with high reliability; an apparatus which can orientate lengths of flexible tubing with respect to rigid commodity members with a high degree of precision; an apparatus for assembling component parts on I.V. tubing utilizing a unique camming system for carrier members to effect a bending of the ends of the tubing; and a machine and apparatus which utilizes an over and under dual conveyor system for assembling component parts on flexible tubing so as to utilize the maximum amount of space required for such an apparatus.

SUMMARY OF THE INVENTION

The foregoing objects are accomplished and the shortcomings of the prior assembling methods for placing components on I.V. tubing are overcome by the present apparatus and method which utilizes first and second conveyor members providing continuous guide paths with means to continuously and simultaneously move each of the conveyors. A frame member supports the conveyors for rotation over a horizontal axis to provide upper and lower loading and unloading surfaces with the first conveyor supported over the second conveyor and portions of the conveyors placed in an overlapping manner. A plurality of tubing clamp members are carried by the first conveyor and a plurality of commodity carrier members are carried by the second conveyor. A feeding and cutting means is associated with the clamp members on the first conveyor to supply predetermined lengths of tubing in the clamp members in a rectilinear manner and in a first plane when the clamp members are positioned at the upper loading surface of the first conveyor. Suitable means are provided to position a commodity in the commodity carrier members. Camming means are arranged in conjunction with the tubing clamp members and the frame to position the ends of the lengths of tubing in a plane other than the first plane. Means are also associated with the tubing clamp members and the commodity carrier members as well as the conveyor members and the frame member to place at least one end of the tubing when in the other plane in the commodity when the tubing clamp members are in the lower unloading position of the first conveyor and the commodity members are in the upper loading position of the second conveyor. In a preferred manner, the first and second conveyor members are defined by two belt members having cleats extending therefrom and engaged by rotatable pulley members having channels for receiving the cleats. Also in a preferable manner, the tubing clamp members have two finger and two holder elements pivotally attached to two oppositely positioned base portions. A camming and scissor action are provided between the finger and holder elements and the clamp body to open and close the fingers and holders around the tubing. In addition, the base portions are pivoted in the clamp body members by camming means cooperatively positioned between the clamp body portion and the frame member. This effects a 90° turn for the tubing when it is held in the finger and holder elements.

BRIEF DESCRIPTION OF THE DRAWINGS

A better understanding of the present assembly apparatus and method for placing component parts are on lengths of I.V. tubing will be had by reference to the drawings wherein:

FIG. 10 is a top view of one of the commodity carrier members with certain portions broken away.

FIG. 11 is a partial view in horizontal section of the carrier member shown in FIG. 10 and in the normal carrying mode for a commodity.

FIG. 12 is a view similar to FIG. 11 except showing the carrier member in a discharge mode.

FIG. 13 is a view taken in vertical section along line 13—13 of FIG. 10.

FIG. 14 is a side elevational view showing a length of tubing after it is cut and positioned by the apparatus of this invention.

FIG. 15 is a view in vertical section of a solvent tray illustrating the tubing shown in FIG. 14 with the ends being placed therein.

FIG. 16 is a view in side elevation depicting the length of tubing shown in FIG. 15 with the excess solvent being removed.

FIG. 17 is a side elevational view illustrating the length of tubing depicted in FIGS. 14–16 being initially positioned in I.V. set components.

FIG. 18 is a view similar to FIG. 17 showing the tubing finally positioned in the components.

DESCRIPTION OF THE PREFERRED EMBODIMENT

Figure 1:
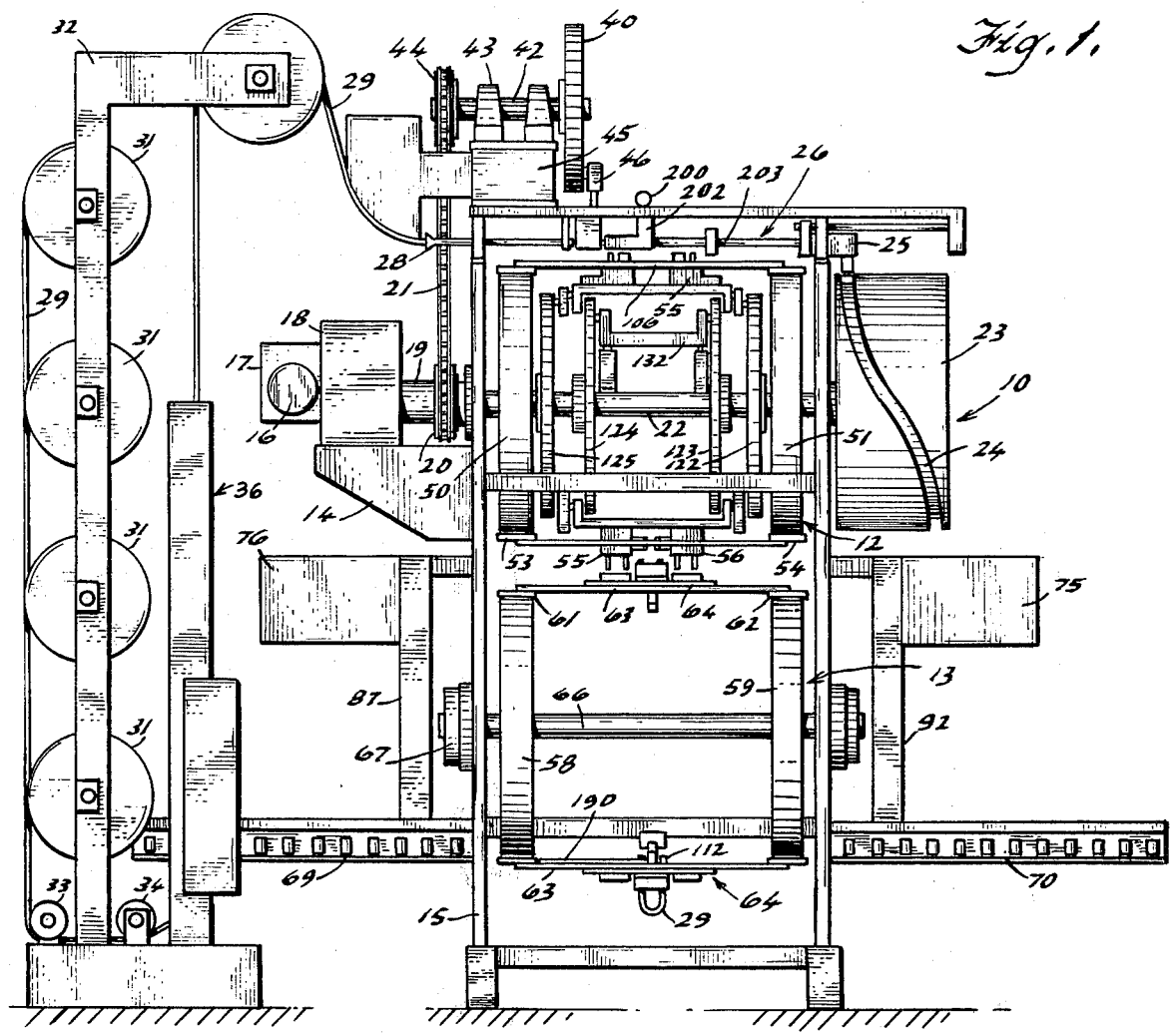
FIG. 1 is an end view of the assembly apparatus of this invention.
Figure 5:
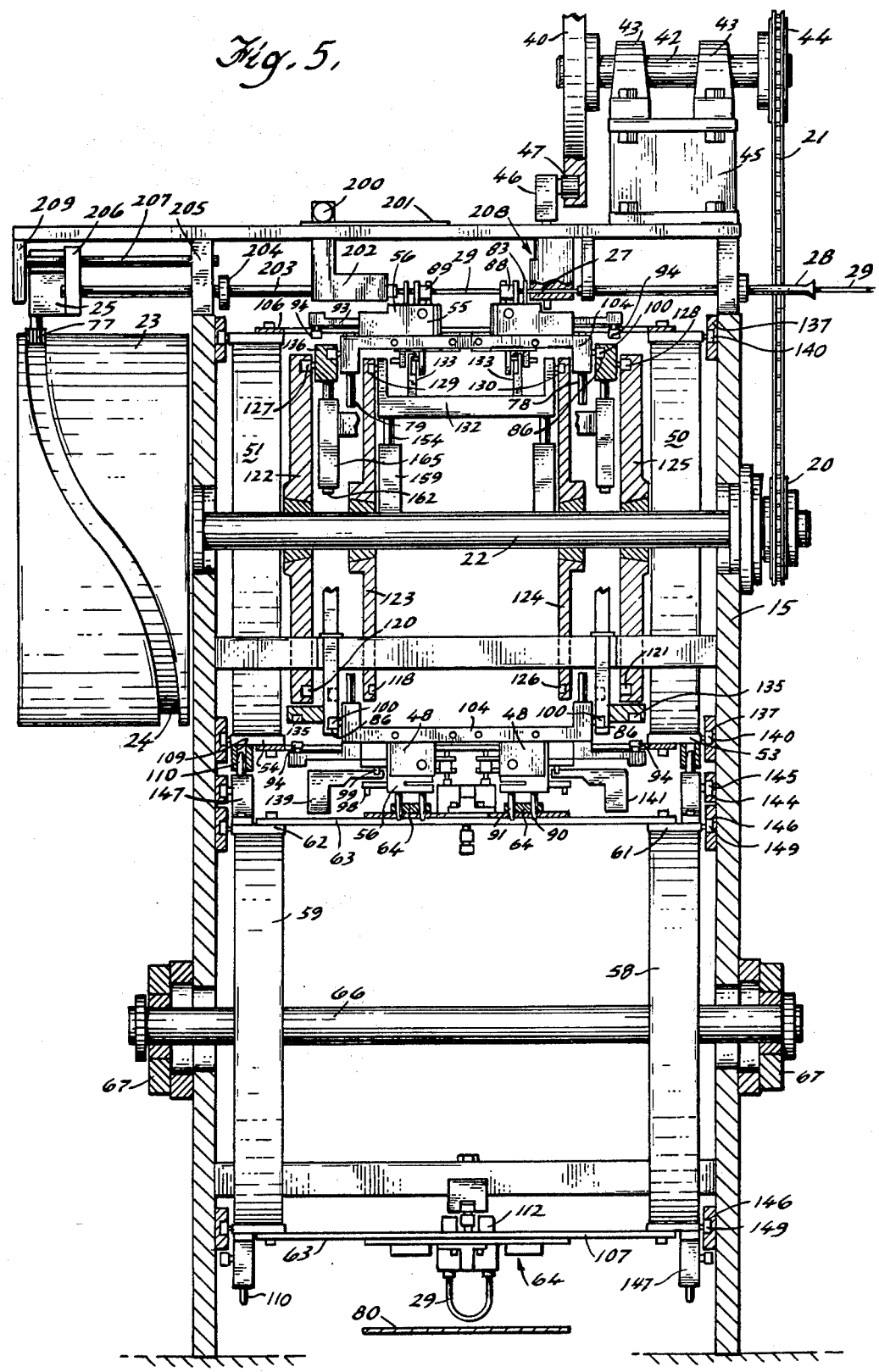
FIG. 5 is an end view opposite to that shown in FIG. 1 and with portions shown in vertical section.
Figure 6:
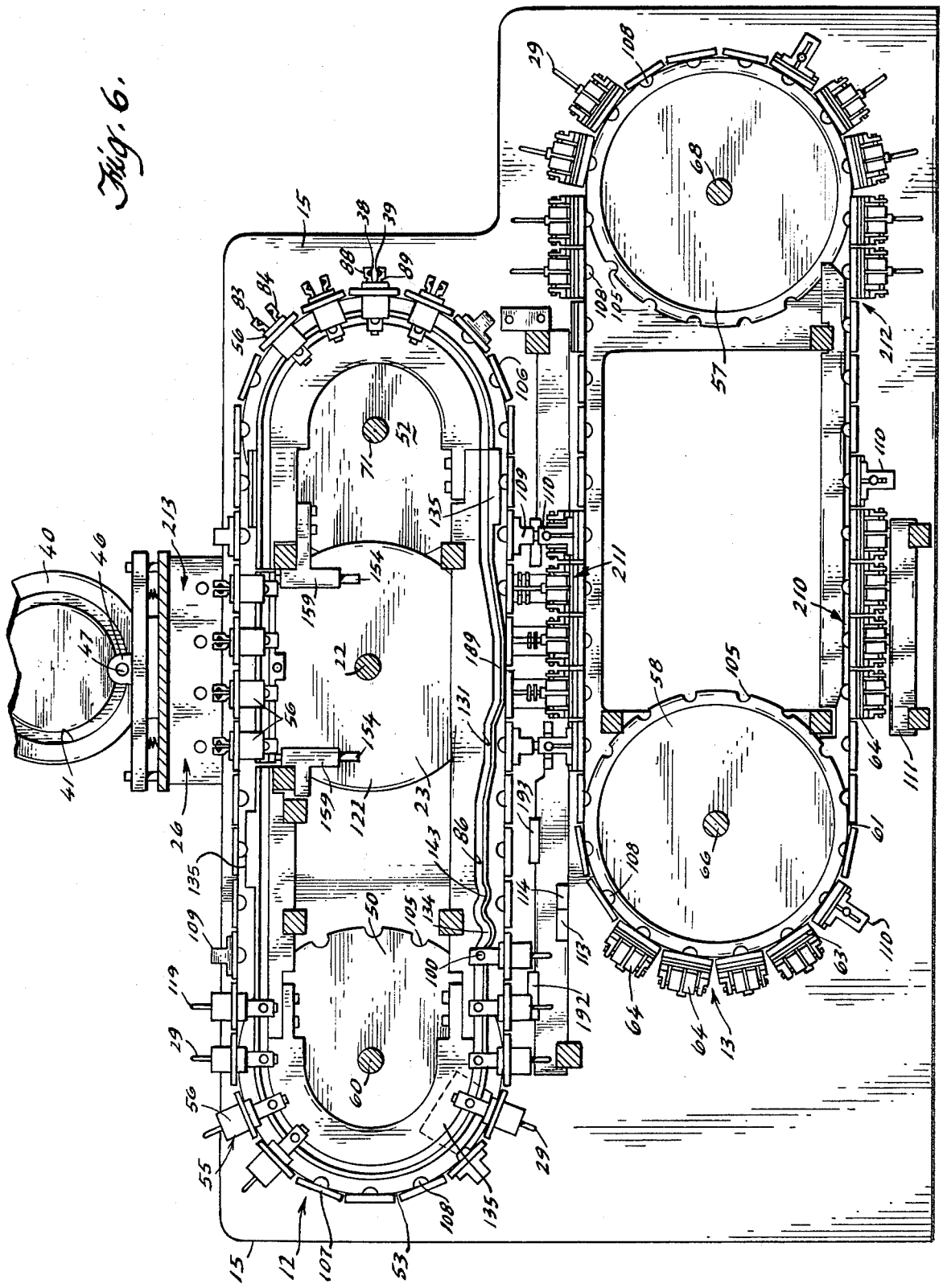
FIG. 6 is a view in vertical section showing the two conveyor systems with one above the other and in an overlapping position.

Proceeding to a detailed description of the invention, and referring particularly to FIGS. 1 and 6, the assembly apparatus generally 10 includes an upper tubing clamp conveyor 12 and the lower commodity conveyor 13. Both of these conveyors are positioned for rotation over a horizontal axis and within a frame 15 having a generally rectangular configuration. Electric motor 16 is utilized in conjunction with a reducer 17 and an index drive 18 to drive both conveyors, as well as a barrel cam 23. This is effected through shaft 19 driving conveyor shaft 71 as well as 22. Disposed on shaft 19 is a sprocket (not shown) which in turn will drive sprocket 20 on shaft 22 by means of chain (not shown). Sprocket 20 will also drive sprocket 44 by means of chain 21. Barrel cam 23 driven by shaft 22 includes a cam track 24 for movement of a cam following member 25 forming a portion of a tube feed assembly generally 26. Also forming a portion of the tube feed assembly is a tubular tube guide 28 for receiving tubing 29. Preferably four tube guide members will be utilized for receiving tubing from rolls 31 suitably supported on frame 32. Guide rollers 33 and 34 assist in the unrolling of the tubing as well as a heater assembly 36 which will aid in placing the tubing in a linear condition. Cam wheel 40 driven by sprocket 44 also composes a portion of tube feed assembly 26. It is driven through shaft 42 suitably supported on bearing supports such as 43 secured to support block 45. As best seen in FIG. 5, cam following member 46 includes a cam roller 47 for rotational and vertical movement in cam wheel 40. Cam follower 46 is in turn interconnected to a tube cutting assembly 208.

Referring specifically to FIG. 6, it will be seen that tubing clamp conveyor 12 includes a pulley member 50 at one end and a driver roller 52 at the opposing end suitably supported in frame 15 by means of shafts 60 and 71. A steel belt 53 will extend over pulley 50 and driver roller 52. It will engage these members through notches such as 105 for engagement with cleats 108 extending from mounting plate 107. In a similar manner, steel belt 61 of commodity conveyor 13 will extend over pulleys 58 and 57 and will drive a belt through mounting plate 107 with cleats 108 for accommodation in notches 105. It will be appreciated that in conjunction with tubing clamp conveyor 12, carrier plate 106 will extend to and be engaged in a similar manner on oppositely positioned pulley 51 and a drive roller (not shown) but which would be driven by drive shaft 71. In a similar manner, in conveyor 13, carrier plate 63 will extend from belts 61 and 62 to be carried over oppositely positioned pulleys 58 and 59 and another pulley member not shown, oppositely disposed from pulley 57 and rotatably carried on shaft 68. It will be noted that commodity carrier 13 is driven through tubing clamp conveyor 12. This is afforded through male guide members 110 on conveyor 13 for engagement in female guide members 109 or conveyor 12. Also shown in FIG. 6 is a solvent station 113 and a dabbing station 114 for purposes of which will be explained in the Operation.

Figure 2:
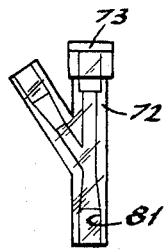
FIG. 2 is a view in side elevation of one of the component parts to be assembled to the flexible tubing.
Figure 3:
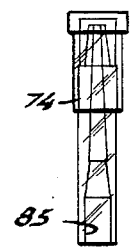
FIG. 3 is a view of the other component part to be assembled.
Figure 4:
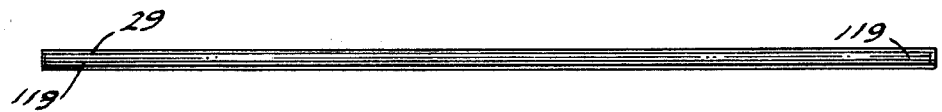
FIG. 4 is a view of a length of flexible tubing to be assembled to the parts shown in FIGS. 2 and 3.

The type of commodities being assembled in the present apparatus are described in FIGS. 2–4. In these figures, a length of tubing 29 is disclosed having opposing ends 119. These ends will be inserted into compartments 81 and 85 of Y-reseal 72 and needle adapter 74 through the action of tubing assembly apparatus 10. These commodities will be fed to commodity conveyors 69 and 70 through commodity supplies 76 and 75 which are schematically shown in FIG. 1. Normally disposed chutes 87 and 92 will provide the necessary interconnection with the usual escapement being provided to drop the products in the pockets. An additional conveyor 80, as best seen in FIG. 5, will transport the finished product from the machine 10.

Figure 7:
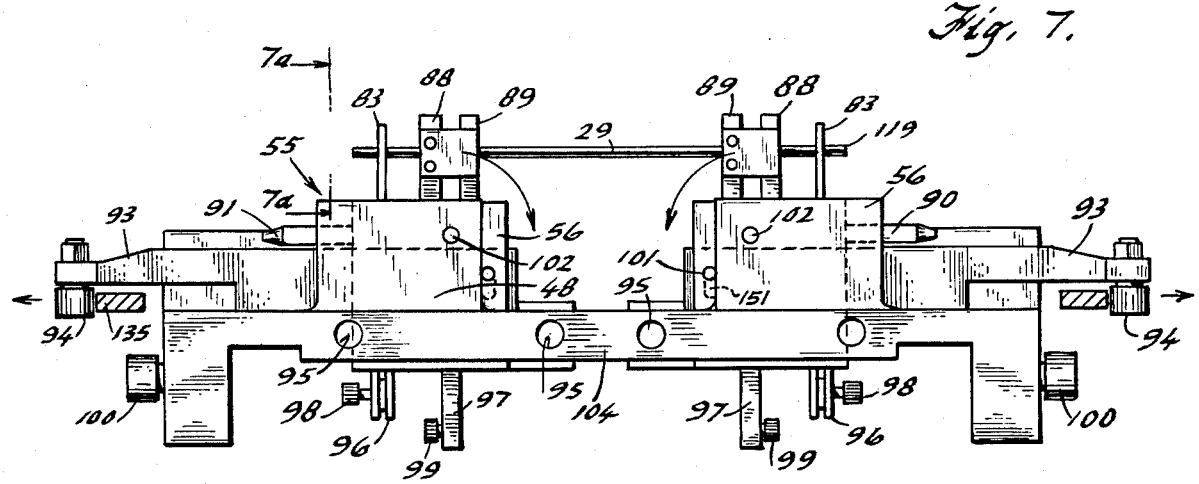
FIG. 7 is a view in side elevation of one of the tubing clamp members immediately after it receives the cut length of tubing.
Figure 7A:
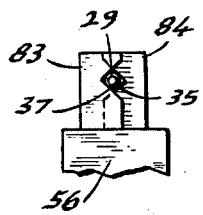
FIG. 7A is a partial view in side elevation illustrating the gripping action of the finger elements engaging the flexible tubing.
Figure 8:
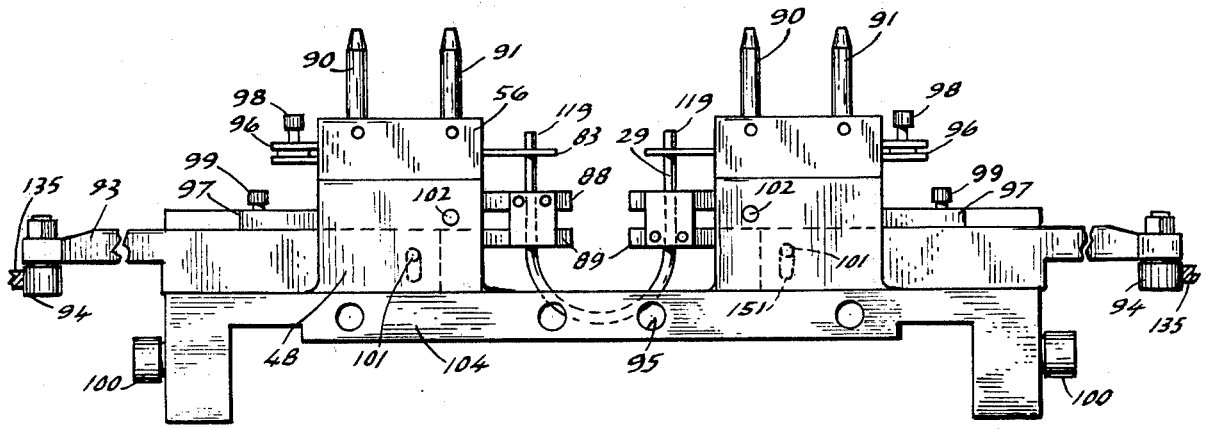
FIG. 8 is a view similar to FIG. 7 except indicating the position of the clamp body members after they have been turned 90°.
Figure 9:
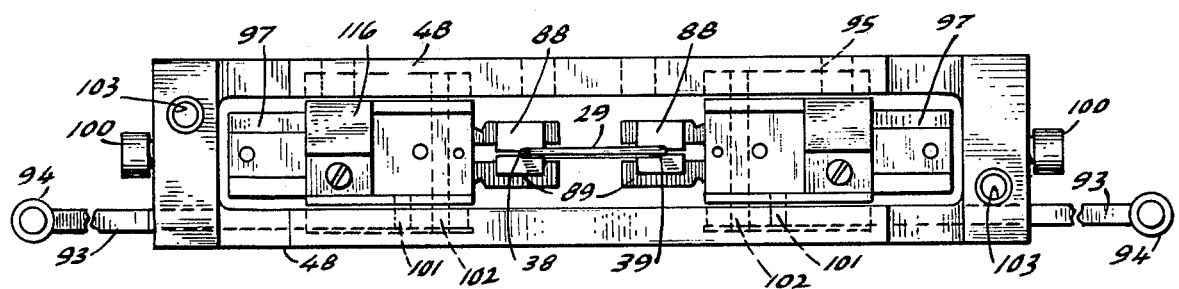
FIG. 9 is a bottom view of the clamp member as shown in FIG. 8.

FIGS. 7–9 illustrate the various parts of the clamp member 55. Each clamp member includes two block-like body portions 56 through which are slidably placed two opposing plate-like overlapping finger elements 83 and 84 having opposing slots 35 and 37 (see FIG. 6) and which are actuated in a scissors-like manner through cam follower arm 96 and cam follower 98. Similarly disposed in block 56 are two oppositely positioned tubing holders 88 and 89 with grooves 38 and 39 to surround tubing 29 which are also disposed through the block for a scissors-like action and actuated by cam follower arm 97 and cam follower 99. Clamp bodies 56 are pivotally secured between support plates 48 by means of pivot pins 102. Attached to clamp bodies 56 are cam follower arms 93 for purposes of providing a 90° rotation of clamp bodies 56. A cam follower 94 is disposed at the end of arm 93 to assist in this rotation which is effected by pin 101 riding in slot 151 of arm 93. Detent openings 95 are provided in base portion 104 to afford a detent mechanism with detents (not shown) carried by clamp bodies 56. Oppositely extending from base portion 104 are two cam followers 100. As best seen in FIG. 9, two guide holes 103 are disposed through base portion 104 for purposes of receiving two post members 78 and 79 (see FIG. 5) which are suitably secured to carrier plate 106. Locating pins 90 and 91 project from clamp bodies 56 for purposes to be later explained.

The movement of the clamp bodies 55 as well as the pocket members 152 and 153 through tubing assembly apparatus 10 are provided by various camming mechanisms therein. In FIGS. 1 and 5, it will be seen that two cam wheels 122 and 125 are rotatably driven by shaft 22. Referring specifically to FIG. 5, it will be seen that cam wheels 122 and 125 have cam tracks 120 and 121 for engagement with cam followers 127 and 128. Similarly supported on shaft 22 are additional cam wheels 123 and 124 having cam tracks 118 and 126 for cam followers 129 and 130, which extend from frame 132 which also carries upwardly extending arms 133. Frame 132 is guided by guide rods 154 through bushing retainer 159. Further cam tracks carried in the apparatus are indicated by the numeral 135 for engagement with cam follower 94 on arm 93 which rotates clamp member 56. Cam tracks 137 are for guidance of cam followers 140 on mounting plate 107 and track 86 for cam follower 100. Cam track 146 provides guidance for cam follower 149 for commodity conveyor 13. Track 144 and follower 145 of holder 147 contains male drive pin 110 for engagement of male drive pin 110 into female pocket member 109.

The commodity carrier generally 64 is specifically described in FIGS. 10-13. It includes a base plate 150 for carrying two oppositely positioned and divided pocket members 152 and 153 having pockets 155 and 156, respectively, with openings 157 and 158. Parting lines 160 and 161 extend between the pocket members for purposes of opening them. Holding members 163 and 164 partially surround the pocket members 152 and 153 and have pins 166 extending therefrom for slidable movement on guide surface 167. A central rod 168 extends between cavities 170 and 171 with springs 169 therein for biasing closed the pocket members 152 and 153 with the springs being seated in cavities 172 of holding members 163 and 164 and support posts 173 and 174. Bolts, such as 175, secure base plate 150 to carrier plate 63. Female plate 176 is secured to base plate 150 with screws 182. Guide holes 185 and 186 are disposed in female plate 176 for engagement with locating pins 90 and 91 of tubing clamp bodies 55. As best shown in FIG. 11, a crank arm 178 extends from the bottom of pocket members 152 and 153 with cam follower 179 rotatably supported thereon. At the opposite end of the crank arm are rollers 180 and 181 for engaging cam surfaces 184 and 183. Rollers 180 and 181 are supported on rotatable member 186 through a bushing 191 extending through base plate 150 and carrier plate 63. Bolt 177 provides the attachment of support posts 173 and 174 to base plate 150. This is best seen in FIG. 13.

FIGS. 14-18 illustrate the steps in the bending of tubing 29 as well as its placement in the solvent adhesive 117 with the ends 119 of tubing 29 being momentarily being placed therein as well as being later contacted on dabbing material 114. FIGS. 17 and 18 illustrate the placement of the treated ends 119 of the tubing in compartments 81 and 85 of Y-reseal 72 and needle adapter 74. FIG. 17 shows the initial placement and FIG. 18 the ultimate seating therein, all being effected by the present apparatus. It should be pointed out that the placement of tubing ends 119 in compartments 81 and 85 is accomplished by the exact positioning afforded by fingers 83 and 84. The use of these fingers is very important as tubing 29 has plastic memory and tends to bend away from the desired position. The opening of the fingers 83 and 84 are effected by engagement with cam followers 98 and cam tracks 192 while a closing is effected by cam tracks 193.

Referring again to FIGS. 1 and 5, it will be noted that the tube feeding and cutting assembly 26 includes a roller member 200 for contacting bearing surface 201 for purposes of supporting tubing holder 202 in the extended position. A pull rod 203 having a stop 204 is interconnected with pull member 206 attached to cam follower member 25, having cam follower 77. A guide rod 207 supports pull member 206 with the guide rod 207 being supported between plates 205 and 209. Also composing a part of the tubing feed mechansim is a tube cutting assembly 208 which is interconnected to cam follower member 46 and cam 47.

OPERATION

A better understanding of the advantages of the tubing assembly apparatus 10 and the method of this invention will be had by a description of the operation of the apparatus.

Flexible I.V. tubing will be supplied from tubing rolls 31 with the tubing being guided past rollers 33 and 34 and in front of heater 36. Tubing will enter tube guide 28 where it will be grasped by tube holder 202. The tubing will be pulled by holder 202 as shown in FIG. 1 and pulled to a position as shown in FIG. 5. This pulling action will be effected as cam follower member 25 with cam follower 77 will be guided in cam track 24 of barrel cam 23. Barrel cam 23 will be rotated through shaft 22 driven by motor 16 as previously explained. A chain will also extend from sprocket 20 on shaft 22 to sprocket 44 for driving shaft 42 and cam wheel 40. The camming action afforded by cam wheel 40 and cam roller 47 will effect a downward movement of tube cutting assembly 208 to effect severance of a length of tubing as it is shown positioned in FIG. 5. It will be appreciated that at all times, four strands of each tubing 29 will be fed into the device and severed with cutting blades mounted on tube cutting assembly 208 engaging lower anvil surfaces such as would be positioned at 27.

During the previously described tube feeding operation, it will be appreciated that tubing clamp converyor 12 and commodity conveyor 13 will be in motion with tubing clamp conveyor 12 assuming a counterclockwise movement as viewed in FIG. 6 and commodity conveyor 13, a clockwise motion. Initial motion is transmitted to drive roller 52 through shaft 71 interconnected to shaft 19 of index drive 18. Drive roller 52, as well as a companion roller journaled on shaft 71 will effect the counterclockwise motion to belts 53 and 54. As this is effected, the female pocket member 109 on conveyor 12 will engage the male drive pin 110 on commodity conveyor 13 to transmit the described clockwise motion to conveyor 13.

Referring to FIG. 6, it will be noted that the clamp bodies 56 will have the finger elements 83 and 84 as well as holders 88 and 89 in an open position as they approach the tube feeding position. The clamp members 55 will be laterally guided throughout their travel on tubing clamp conveyor 12 by cam track 86 and engagement with cam follower 100. When members 55 reach the position immediately below tube feed assembly 26 they will be moved from the lower position shown in FIG. 1 to a raised position as shown in FIG. 5 through cam track assembly carriage 136. This is effected by cam followers 127 and 128 riding in cam wheels 122 and 125 with cam followers 100 of base portion 104 engaged in the cam track section 136. Cam track section 136 is guided by pins 162 in housing holders 165. In the raised position, tubing 29 will be fed between the holders 88 and 89 as well as fingers 83 and 84 of opposing clamp bodies 56. At this stage holders 88 and 89 will be closed around tubing 29 by arms 133 engaging cam followers 99 and exerting a downward force thereon when frame 132 is moved downwardly through the movement of cam followers 129 and 130 riding in cam wheels 123 and 124. With the tubing 29 held in place tube cutting assembly 208 is actuated by a slight downward movement of cam follower member 46 as effected by cam roller 47 riding in cam wheel 40. This will sever the tubing and further rotation of cam wheels 122 and 125 will return clamp bodies 56 to their original down position.

Upon leaving the feeding station, clamp bodies 56 will be rotated 90 degrees as cam follower arms 93 are cammed laterally by cam followers 94 and cam tracks 135 from a position shown in FIG. 7 to that shown in FIG. 8. In this position, the tubing will have been bent into a U-shape configuration as shown in FIG. 8 with the ends 119 directed upwardly. The clamp members will continue in their travel downwardly over pulley members 50 and 51 to the lower section of tubing clamp conveyor 12 where the ends 119 of the tubing will be in an inverted position and row-like manner. As cam followers 100 travel over depressed portions 134 and 143 of cam tracks 86, the ends 119 of the tubing 29 will be placed in solvent tray 113 and then dabbing tray 114. The solvent in tray 113 is vinyl methylene chloride solution and will act as an adhesive in that it is a partial solvent for the tubing. Upon leaving this area cam followers 100 will next encounter a further depressed portion in cam tracks 86 as shown at 131. At this point, the ends of tubing 29 will be moved partially into Y-reseal 72 and needle adapter 74. At depressed portion 189 the clamp bodies 56 will be moved into their lowest position to complete the insertion of the tubing as shown in FIG. 18. Meanwhile, Y-reseal 72 and needle adapter 74 will be carried by commodity carriers 64 as will now be explained.

Simultaneously with the counterclockwise movement of tubing clamp conveyor 12, commodity conveyor 13 will be moved in a clockwise manner as previously explained. For this purpose it will be noted that at any given cycle of conveyors 12 and 13, two of members 109 and 110 are in contact. Referring to FIG. 1, Y-reseal components will be contained in commodity supply container 76 and needle adapters 74 will be contained in commodity supply container 75. Supply chutes 87 and 92 will direct these components downwardly into commodity conveyors 69 and 70 which place them in pockets 155 and 156 of commodity carrier 64. This placement will be effected by means of a shuttle plate 190 which is arranged to drop the components from pockets in conveyors 69 and 70 into the respective open position of pockets 155 and 156 of commodity carrier 64 (FIG. 12). This positioning and orientation will be added by underlying stop block 111. The opening of the pockets 155 and 156 to receive the commodities will be accomplished by a suitable lateral camming of cam followers 179 to effect rotation of rotatable member 186 and movement of cam rollers 180 and 181 against cam surfaces 183 and 184. The commodities will be captured in cavities 155 and 156 when cam follower 179 no longer is in contact with a suitably positioned camming surface such as 112 and pocket members 152 and 153 will close through the force of springs 169. From the loading station 210 the commodity carriers 64 are moved on conveyor 13 to the insert station 211 where the ends 119 of tubing 29 will be placed in Y-reseal 72 and needle adapter 74 when clamp members 55 are in the previously described depressed track portions 131 and 189. This precise placement will be effected in part by guide pins 90 and 91 entering guide holes 185 and 188 of commodity carriers 64 as well as the use of fingers 83 and 84. After the ends 119 are placed in the respective compartments 81 and 85, fingers 83 and 84 and holders 88 and 89 will release their grip on the tubing by means of suitable camming action on cam followers 98 and 99. Commodity carriers will continue their travel to an unload station 212 wherein the finished component will be released from pockets 155 and 156 of commodity carrier 64 by the previously described camming of cam follower 179 and fall onto conveyor 80.

The clamp bodies 56 will continue in their travel on conveyor 12 where cam followers 94 will engage camming surfaces 135 except oppositely positioned to return clamp bodies 56 to the position shown in FIG. 7 with fingers 83, 84 and holders 88, 89 directed away from base portion 104. The fingers and holders will then be in position to receive tubing 29 at tube feeding station 213. The cycle is then repeated.

All of the drive components such as motor 16, reducer 17 and index drive 18 are standard components. For example, motor 16 is a 1½ H.P., D.C. motor and reducer 17 is a 60-to-1 reduction unit, both available from commercial sources as is index drive 18 which is a 2-stop parallel index drive unit.

Infeed commodity conveyors 69 and 70 are custom built and available from Custom Tool and Machinery, Inc. of Kenosha, Wis. Commodity supply containers 75 and 76 are of the vibratory bowl type available commercially. The feed conveyor systems are synchronized with the movement of conveyors 12 and 13 by a chain drive from shaft 68 to a 2-stop index unit which in turn drives the commodity conveyors through an 8-to-1 ratio, utilizing suitable vertical drive shafts and pulleys.

Tubing assembly apparatus 10 is a high capacity machine. Under normal conditions, it can assemble 20,000 finished units in eight hours. The only operating supervision is to inspect finished product and perform normal machine attendance.

It will thus be seen that there is now provided a fully automated assembly machine which can receive flexible tubing from a supply roll, cut it, bend it, treat the ends with an adhesive and insert them into commodities. All this is effected with precision in that very few rejected parts result. While specific commodities have been illustrated for placement on a length of tubing, it will be appreciated that the tubing assembly machine is capable of adjustment to receive commodities of various geometric configurations as well as tubing of various sizes.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. An apparatus for assembling component parts to lengths of flexible tubing comprising:
    a first and a second conveyor member, each said conveyor member defined by a continuous guide path;
    means to continuously move each said conveyor;
    a frame member supporting said conveyors for rotation over a horizontal axis to provide upper and lower loading and unloading surfaces with said first conveyor supported above said second conveyor with portions of said conveyors placed in an overlapping manner;
    a plurality of oppositely positioned tubing clamp members carried by said first conveyor;
    a plurality of commodity carrier members carried by said second conveyor;
    means operatively associated with said tubing clamp members to supply predetermined lengths of tubing in said tubing clamp members in a rectilinear manner and in a first plane when said clamp members are positioned at said upper loading surface of said first conveyor;

means operatively associated with said commodity members to position a commodity thereon;

means constructed and arranged in conjunction with said tubing clamp members and said frame member to position the ends of said lengths of tubing in a plane other than said first plane; and means operatively associated with said tubing clamp members, said commodity carrier members, said conveyor members and said frame member to place at least one end of said tubing when in said other plane in said commodity when said tubing clamp members are in the lower unloading position of said first conveyor and said commodity carrier members are in the upper loading position of said second conveyor.

2. The apparatus for assembling component parts as defined in claim 1 wherein said means constructed and arranged in conjunction with said tubing clamp members and said frame member to position the ends of said lengths of tubing in a plane other than said first plane is defined by a camming means operatively positioned between said tubing clamp member and said frame member.

3. The apparatus for assembling component parts as defined in claim 2 wherein said tubing clamp members are defined by a base portion secured to said first conveyor and pivotally attached to said base portion, said camming means defined by a cam follower extending from said clamp body portion and a cam track operatively carried by said frame member.

4. The apparatus for assembling component parts as defined in claim 3 wherein said tubing clamp members are defined by two finger elements pivotally attached to said clamp body portion and further including camming means operatively associated with said finger elements and said frame member to move said finger elements from open and closed positions over said tubing.

5. The apparatus for assembling component parts as defined in claim 4 wherein said tubing clamp members further include two holding members for said tubing axially and pivotally positioned with respect to said two finger elements and secured to said clamp body portion; and additional camming means operatively associated with said holding members and said frame member to move said holding members from open and closed positions over said tubing.

6. The apparatus for assembling component parts as defined in claim 2 wherein said first and second conveyor members are defined by two belt members having cleats extending therefrom and rotatable pulley members having channels for receiving said cleats.

7. The apparatus for assembling component parts as defined in claim 6 further including fluid reservoir means for a liquid solvent, said reservoir means operatively positioned adjacent the path of travel of said lower unloading surface of said first conveyor and camming means operatively positioned between said tubing clamp member and said frame member to move said clamp members toward and away from said reservoir means.

8. The apparatus for assembling component parts as defined in claim 7 further including a solvent removal means operatively positioned downstream of said reservoir means for said liquid solvent and camming means operatively positioned between said tubing clamp member and said frame member to move said clamp members toward and away from said solvent removal means.

9. The apparatus for assembling component parts as defined in claim 8 wherein said tubing clamp members include projecting orientation means and said commodity carrier members include accommodating apertures for said projecting orientation means.

10. The apparatus for assembling component parts as defined in claim 1 wherein said means to supply predetermined cut lengths of tubing in said clamp members is defined by a combined tube drawing and cutting mechanism.

11. The apparatus for assembling component parts as defined in claim 10 further including means to supply said tubing from spool members to said combined tube drawing and cutting mechanism.

* * * * *